United States Patent [19]

Watson

[11] Patent Number: Plant 6,039

[45] Date of Patent: Oct. 20, 1987

[54] AMELANCHIER TREE NAME "PRINCE CHARLES"

[76] Inventor: Thomas Watson, 1746 Highway 73, Cambridge, Wis. 53523

[21] Appl. No.: 705,615

[22] Filed: Feb. 26, 1985

[51] Int. Cl.[4] ..... A01H 5/00

[52] U.S. Cl. ..... Plt./51

[58] Field of Search ..... Plt. 51

[56] References Cited

U.S. PATENT DOCUMENTS

P.P. 3,092 4/1972 Flemer ..... Plt. 51

OTHER PUBLICATIONS

DeWolf, Gordon, "Shadbush" *Horticulture,* vol. 60, No. 5, p. 22, May, 1982.

Weaver, Richard E., Jr., "The Shadbushes" *Arnoldia,* vol. 34, No. 1, (1974), pp. 22–31.

Elias, T. S., *Trees of North America,* pub. Outdoor Life/-Nature Books: Van Nostrand Reinhold Company, (1980), p. 596 only.

Fernald, M. L., *Gray's Manual of Botany,* (8th Ed.), (1950), Harvard College President and Fellows, p. 767 only.

Hillier, H. G., *Hillier's Manual of Trees and Shrubs,* (2nd Ed.), A. S. Barnes and Company, (1979), p. 31 only.

Rehder, Alfred, *Manual of Cultivated Trees and Shrubs,* (2nd Ed.), Macmillan Company, N.Y., (1960), p. 389 only.

*Primary Examiner*—James R. Feyrer

*Attorney, Agent, or Firm*—Isaksen, Lathrop, Esch, Hart & Clark

[57] ABSTRACT

A new variety of *Amelanchier laevis* is disclosed which is particularly characterized by its trait of achieving maximum floral display prior to the unfolding of its leaves so as to maximize the color display during the blossom period.

3 Drawing Figures

The present invention relates to a new and distinct variety of Amelanchier believed to be *Amelanchier laevis* which was found in a cultivated area.

The distinct characteristics of the tree of the present invention is that white flowers unfold before leaves unfold, therefore giving a better flower display than other varieties of *Amelanchier laevis* in which varieties the leaves unfold prior to or simultaneous with the flowers. The leaves of the new variety are glabrous on the underside, bronze in coloration, and do not have hairs.

Asexual reproduction of the new variety was accomplished by tissue culture of new bud cells, and showed that the foregoing characteristics and distinctions come true to form and are established and transmitted through succeeding propagations.

The accompanying drawing shows a typical tree specimen of the new variety, together with typical foliage and flower specimens on a larger scale.

The following is a detailed description of the new variety, with color terminology in accordance with the Inter-Society Color Council — National Bureau of Standards, Circular 553, Color Chart, except where general color terms of ordinary dictionary significance are obvious.

Parentage: Bud cells.
- *Seed parents.*—Two unknown Amelanchiers both believed to be varieties of *Amelanchier laevis.*

Propagation: Holds its distinguishing characteristics through succeeding propagations by tissue culture.

Locality where discovered: University of Wisconsin Arboretum, Madison, Wis.

Locality where propagated and grown: Cambridge, Wis.

Tree: Slender, upright, grows to an average of 25–30 feet tall.

Trunk: Slender; smooth.
- *Color.*—Brown-Gray, Hue No. 64.

Branches: Smooth.
- *Color.*—Grayish Brown, Hue No. 61.

Foliage:
- *Leaves.*—Thick.
- *Quantity.*—Moderate.
- *Length.*—average 7 cm.
- *Width.*—Average 4 cm.
- *Shape.*—Oval-lanceolate.
- *Color.*—Upper surface medium olive green, Hue No. 125; under surface — medium yellow green, Hue No. 120.
- *Margin.*—Serrate; serrations about 1 mm deep and average 0.3 cm apart.
- *Petiole.*—Average 2 cm long. Unfolding new leaves are glabrous on underside and bronze coloration similar to Hue No. 40.

Flower buds:
- *Hardiness.*—−30° F.
- *Size.*—Length average 0.9 cm. Width average 0.3 cm.
- *Shape.*—Globular.
- *Color.*—White; Hue No. 263.

Flowers:
- *Quantity.*—Abundant average April 25.
- *Size.*—Average 2 cm in diameter.
- *Petalage.*—5 petals. Shape — rounded. Size: Length, average 1 cm; Width, average 0.6 cm. Color: White; Hue No. 263.

Fruits:
- *Borne.*—Average June 20 to July 1.
- *Abundance.*—Abundant.
- *Shape.*—Globular.
- *Size.*—Length average 0.8 cm. Width average 0.9 cm.
- *Color.*—Very deep red purple; Hue No. 243.

Winter buds: Narrow, pointed, light brown; Hue No. 58.

I claim:

1. A new and distinct variety of *Amelanchier laevis,* substantially as herein shown and described, characterized particularly as to novelty by unfolding flowers prior to unfolding leaves.

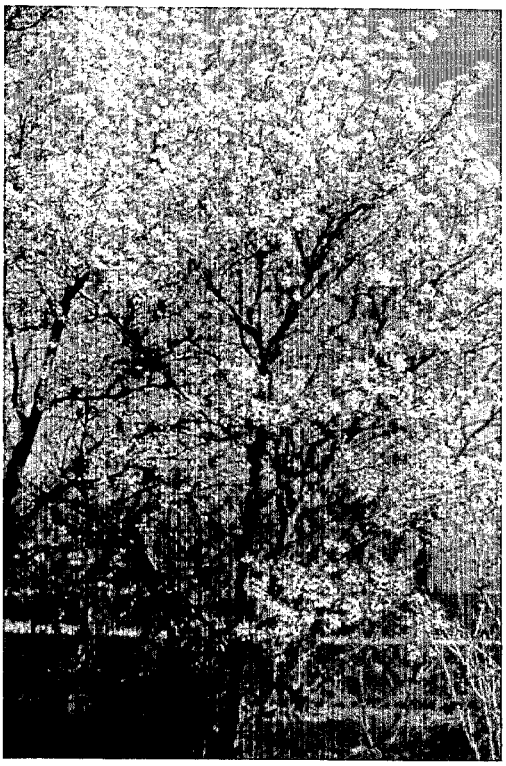
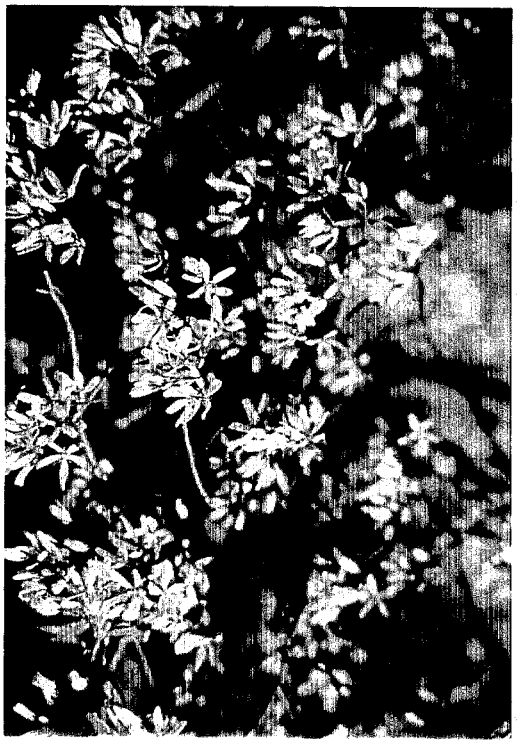
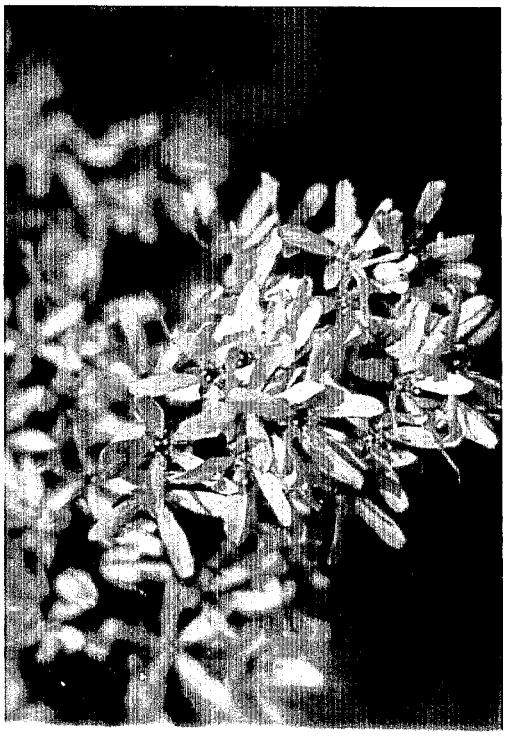

* * * * *